United States Patent [19]
Chen

[11] Patent Number: 5,264,346
[45] Date of Patent: Nov. 23, 1993

[54] COLORIMETRIC METHOD FOR BETA-LACTAMASE ASSAY AND ITS APPLICATIONS

[76] Inventor: Kirk C. S. Chen, 543 NE. 79th St., Seattle, Wash. 98115

[21] Appl. No.: 710,510

[22] Filed: Jun. 3, 1991

[51] Int. Cl.$^5$ .......................... C12Q 1/26; C12Q 1/28
[52] U.S. Cl. ........................................... 435/25; 435/4; 435/18; 435/28; 435/32; 435/39; 435/47; 435/49; 435/231; 435/871; 435/933; 435/973; 436/73; 436/904; 514/192; 514/200
[58] Field of Search ................ 435/28, 4, 18, 25, 32, 435/39, 47, 49, 231, 871, 933, 973; 436/73, 904; 514/192, 200

[56] References Cited

U.S. PATENT DOCUMENTS

| | | | |
|---|---|---|---|
| 3,876,503 | 4/1975 | Mennen | 195/103.5 R |
| 3,954,563 | 5/1976 | Mennen | 195/127 |
| 3,954,564 | 5/1976 | Mennen | 195/127 |
| 4,018,653 | 4/1977 | Mennen | 195/127 |
| 4,108,729 | 8/1978 | Mennen | 195/127 |
| 4,355,113 | 10/1982 | Mennen | 435/810 |
| 4,740,459 | 4/1988 | Chen et al. | 435/18 |
| 4,965,193 | 10/1990 | Chen | 435/18 |

OTHER PUBLICATIONS

Ross et al, *Methods in Enzymology*, vol. 43, pp. 69–85, (1975).
Levine *Nature*, vol. 187, pp. 939–940, 1960.
Novick, *Biochem. J.*, vol. 83, pp. 236–240, 1962.
Sykes et al. *Antimicrob. Agents Chemother.*, vol. 1, No. 2, pp. 94–99, 1972.
Lonyi, *Methods in Microbiology*, vol. 19, pp. 18–21 and 64–67.
Philips, *Lancet II*, pp. 656–657 (1976).
Ashford et al, *Lancet II*; pp. 657–658 (1976).
Morbid, *Mortal. Weekly Rep.* vol. 36, No. 8, pp. 107–108, 1987.
Morbid, *Mortal. Weekly Rep.*, vol. 39, No. 17, pp. 284–287, 1987.
Sng et al. *Br. J. Vener. Dis.*, vol. 60, pp. 374–379, 1984.
Kraus et al, *Sex. Transm. Dis.*, vol. 15, No. 4, pp. 234–243, 1988.
Steel et al, *J. Gen. Microbiol.*, vol. 25, pp. 297–306, 1961.
Janda et al, *J. Clin. Microbiol.*, vol. 21, No. 2, pp. 143–145, 1985.

(List continued on next page.)

*Primary Examiner*—Michael G. Wityshyn
*Assistant Examiner*—Abdel A. Mohamed

[57] ABSTRACT

A novel colorimetric method for beta-lactamase assay and its applications are disclosed. The novel assay method for beta-lactamase is based on the discovery described in this invention. The chromophore formed by oxidation of either the N-alkyl derivative of p-phenylenediamine or the 3,3',5,5'-tetraalkyl derivative of benzidine can be decolorized by the open beta-lactam ring end product resulting from the hydrolysis of a penicillin in the presence of a mercury-containing compound. The same chromophore can be decolorized by the open beta-lactam ring end product resulting from the hydrolysis of a cephalosporin in either the presence or the absence of the mercury-containing compound. None of the intact beta-lactam antibiotics can decolorize the chromophore in either the presence or the absence of the mercury-containing compound. The final concentration of the mercury-containing compound in the decolorization mixture ranges from approximately 0.005 mM to approximately 3 mM, and the pH of the decolorization mixture ranges from 3.5 to 8.0. Additional applications derived from coupling this novel assay method to methods in the art include: a method for specific detection of microbial beta-lactamases; a method for simultaneous detection of microbial cytochrome c oxidase systems and penicillinases, and its application to simultaneous presumptive identification of *Neisseria gonorrhoeae* in urethral exudates, and differentiation of the infecting gonococci into penicillinase-producing *N. gonorrhoeae* and non-penicillinase-producing *N. gonorrhoeae*; and a simultaneous assay method for peroxidase and penicillinase.

19 Claims, 7 Drawing Sheets

OTHER PUBLICATIONS

Chen et al, *J. Clin. Microbiol.*, vol. 23, No1 3, pp. 539-544, 1986.

Taylor et al, *Lancet* II, pp. 625-626, 1985.

Yolken, et al, *J. Immunol. Methods*, vol. 73, pp. 109-123, 1984.

Chen, *Antimicrob. Agents and Chemother.*, vol. 30, No. 4, pp. 536-541, 1986.

Larock, "Organomercury Compounds in Organic Synthesis; Reactivity and Structure Concepts in Organic Chemistry", vol. 22, pp. 4-154 (1985).

Josephy et al, *J. Biol. Chem.*, vol. 257, No. 7. pp. 3669-3675, 1982.

Chen et al, *J. Clin. Microbiol.*, vol. 19, No. 6, pp. 818-825, 1984.

Davis et al, *Biochem. J.* vol. 143, pp. 129-135, 1974.

Kaj André Hohn, *Anal. Chem.*, vol. 44, No. 4, pp. 795-799, 1972.

Summary of the procedure for simultaneous detection of microbial cytochrome c oxidase system and penicillinase using the peroxidase-chromophore decolorization method (1) Detection of cytochrome c oxidase system:

The blank: Combined substrate solution + Buffer only ———————→ A°

The test: Combined substrate solution + Buffer containing ———————→ A
the organism Combined substrate solution: Solution containing the oxidase reagent, TMP and a penicillin; A°: Color intensity of the blank; A: Color intensity of the test.

Interpretation: A greater than A°, oxidase positive; A same as A°, oxidase negative. Add exotic P-CHR-TMP to the test, if oxidase test is negative or weak-positive.

(2) Detection of penicillinase:

The blank: Aliquot of the test from (1) + buffer only ———————→ A'°

The test: Aliquot of the test from (1) + buffer containing a ———————→ A'
decolorization enhancer A'°: Color intensity of the blank; A': Color intensity of the test.

Interpretation: A'° greater than A', penicillinase positive; A'° same as A', penicillinase negative.

FIG. 4

Summary of the procedure for simultaneous presumptive identification of Neisseria gonorrhoea in urethral exudates and differentiation of the infecting gonococci into penicillinase-producing N. gonorrhoeae (PPNG) and non-penicillinase-producing N. gonorrhoeae (non-PPNG) using the peroxidase-chromophore decolorization method (1) Presumptive identification of Neisseria gonorrhoeae:

The blank: Combined substrate solution + Swab only 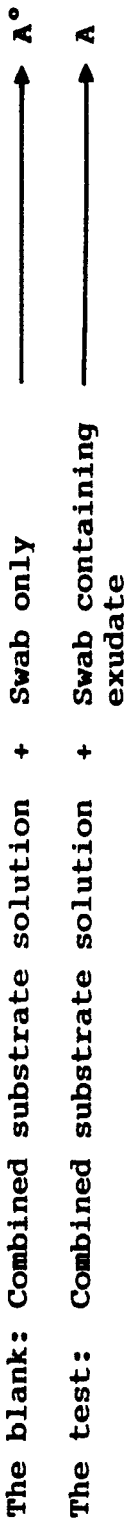 A°

The test: Combined substrate solution + Swab containing exudate 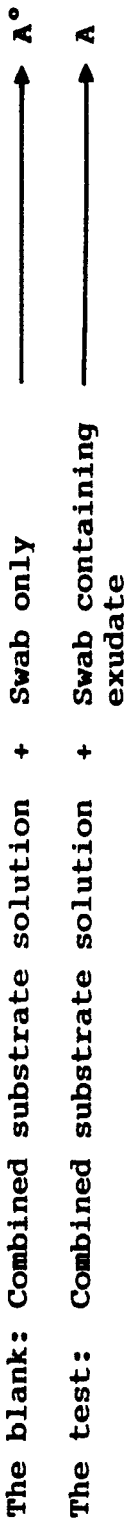 A

Combined substrate solution: Solution containing the oxidase reagent, TMP and a penicillin; A°: Color intensity of the blank; A: Color intensity of the test.

Interpretation: A greater than A°, oxidase positive-presumptive identification of N. gonorrhoeae; A same as A°, oxidase negative-non-gonococcal infection.

(2) Presumptive differentiation of the infecting gonococci into PPNG and non-PPNG:

The blank: Aliquot of the test from (1) + Filter paper  A'°

The test: Aliquot of the test from (1) + Treated filter paper  A'

Treated filter paper: Filter paper impregnated with a decolorization enhancer; A'°: Color intensity of the spot on the untreated filter paper; A': Color intensity of the spot on the treated filter paper.

Interpretation: A'° greater than A', penicillinase positive-presumptive PPNG infection; A'° same as A', penicillinase negative-presumptive non-PPNG infection.

FIG. 5

Summary of the procedure for simultaneous assay of peroxidase and
penicillinase using the peroxidase-chromophore decolorization method (1) Peroxidase assay:

The blank: Combined substrate solution + Buffer only ⟶ A°

The test: Combined substrate solution + Buffer containing ⟶ A
combined enzymes

Combined substrate solution: Substrate solution containing a peroxidase-chromogen
(TMB or TMP)/$H_2O_2$ and a penicillin; Combined enzymes: Peroxidase and penicillinase;
A°: Absorbance of the blank; A: Absorbance of the test.

Quantitation: Using the standard curve of increase in absorbance (A−A°) vs.
the amount of peroxidase.

(2) Penicillinase assay:

Assay mixture from (1) $\xrightarrow{\text{Exotic peroxidase}}$ A' $\xrightarrow{\text{Catalase}}$ $\xrightarrow{\text{Decolorization enhancer}}$ A''

A': Absorbance of either the blank or the test from (1), in which the residual
peroxidase-chromogen is further oxidized with exotic peroxidase and the resulting
peroxidase-chromophore is stabilized by catalase; A'': Absorbance of the mixture
with A' after addition of a decolorization enhancer; the absorbance of the
resulting mixture is corrected for dilution.

Quantitation: For penicillinase activity, using the standard curve of decolorization
(A'−A'') vs. the concentration of the open beta-lactam ring end product and the standard
curve of the concentration of the open beta-lactam ring end product vs. the amount of
penicillinase.

FIG. 6

COLORIMETRIC METHOD FOR BETA-LACTAMASE ASSAY AND ITS APPLICATIONS

BACKGROUND OF THE INVENTION

1. Field of the Invention

This invention relates to a novel colorimetric method for beta-lactamase assay and its applications.

2. Description of the Prior Art

The amide bond in a beta-lactam ring of a beta-lactam antibiotic can be hydrolyzed enzymatically by beta-lactamases or non-enzymatically in neutral or alkaline aqueous solution to form an open beta-lactam ring end product. The open beta-lactam ring end product resulting from the hydrolysis of a penicillin, catalyzed by beta-lactamase, is the corresponding penicilloic acid, which is stable; while that resulting from the hydrolysis of a cephalosporin is the corresponding cephalosporoic acid, which is often unstable [Ross G. W., and C. H. O'Callaghan, Methods in Enzymology 43: 69-85 (1975)]. When the beta-lactam ring of a penicillin is hydrolyzed non-enzymatically, the corresponding penicilloic acid is a mixture of its diastereomers [Levine, B. B., Nature 187: 939-940 (1960)]. The iodometric method is one of the colorimetric methods developed for qualitative or quantitative assay of beta-lactamase. It is based on the decolorization of a chromophore by the open beta-lactam ring end product, but not by its intact beta-lactam substrate. A microiodometric method which employs a starch-iodine complex as the chromophore is widely used for beta-lactamase assay [Novick, R. P., Biochem. J. 83: 236-240 (1962); Sykes, R. B., and K. Nordstrom, Antimicrob. Agents Chemother. 1: 94-99 (1972)]. However, since the iodine molecules in the iodine-starch complex sometimes inactivate the enzyme, the microiodometric method cannot be used universally for beta-lactamase assay. The newly developed fluorescence assay methods and several other methods for detection of microbial beta-lactamases have been described in U.S. Pat. Nos. 4,740,459 (1988) to Chen, K. C. S., J. Knapp and K. K. Holmes; and 4,965,193 (1990) to Chen, K. C. S. Although the fluorescence assay methods disclosed in the previous patents are sensitive and specific for detecting microbial beta-lactamases, they all require a long-wave ultraviolet lamp and a dark chamber for viewing the fluorescent end products.

The cytochrome c oxidase test (known as the oxidase test) is a procedure for detecting the presence of the cytochrome c oxidase system in bacteria, and is important in identifying and/or differentiating certain microorganisms. In the oxidase test, cytochrome c oxidase catalyzes the oxidation of reduced cytochrome c by molecular oxygen. The test reagent, an N-alkyl derivative of p-phenylenediamine such as N,N-dimethyl-p-phenylenediamine (DMP), or N,N,N',N'-tetramethyl-p-phenylenediamine (TMP), is then oxidized to a colored compound by the oxidized cytochrome c, which in turn changes to reduced cytochrome c [Lanyi, B., Methods in Microbiology 19: 1-67 (1987)]. Some oxidase-positive microorganisms also produce penicillinases. Current methods require two separate tests for detecting the microbial cytochrome c oxidase system and penicillinase.

Gonorrhea remains one of the most widespread sexually transmitted diseases in the world. Since strains of the penicillinase-producing Neisseria gonorrhoeae (PPNG) were first isolated in 1976 [Phillips, I., Lancet ii: 656-657 (1976); Ashford, W. A. et al., Lancet ii: 657-658 (1976)], gonococcal infections caused by PPNG have increased dramatically in the United States and other parts of the world. In 1986, PPNG infections accounted for approximately 2% of gonorrhea reported in the United States [Morbid. Mortal. Weekly Rep. 36: 107-108 (1987)] and in 1988 and 1989, PPNG accounted for 3.2% and 7.4% of the isolates, respectively, at 21 selected public clinics in 21 major U.S. cities [Morbid. Mortal. Weekly Rep. 39: 284-287 (1990)]. In Southeast Asia, the isolation rates of PPNG strains have remained high. The incidences in several countries were recorded as follows: Japan 16.1%; Malaysia 37.2%; Thailand 42%; South Korea 40+%; the Philippines 30-40%; Indonesia 25%; and Singapore 25% [Sng, E. H. et al., Br. J. Vener. Dis. 60: 374-379 (1984)]. With the exception of allergic reactions, penicillin antibiotics are free of adverse side effects and relatively inexpensive for treating gonorrhea, but they cannot be used to eradicate PPNG. Instead, more expensive drugs which often require parenteral administration and cannot eradicate coexisting syphilis, are employed [Kraus, S. J. et al., Sex. Transm. Dis. 15: 234-243 (1988)].

Gonorrhea is diagnosed by the recognition of typical Gram-negative intracellular diplococci in stained smears and by identification of N. gonorrhoeae in cultures of secretions. In a clinical laboratory, identification of N. gonorrhoeae in urethral exudates requires culture of the organism, which takes approximately 24-72 hours. Differentiation of the infecting gonococci into PPNG and non-PPNG requires further testing for penicillinase production after culture. Because of the time necessary for analysis, the outcome of the laboratory testing is rarely of use to the physician in initial therapy. Therefore, most patients are treated empirically on the basis of a Gram stain. The oxidase test has long been used for identifying N. gonorrhoeae [Steel K. J., J. Gen. Microbiol. 25: 297-306 (1961)]. U.S. Pat. Nos. 3,876,503 (1975), 3,954,563 (1976), 3,954,564 (1976), 4,018,653 (1977), 4,108,729 (1978), 4,340,670 (1982) and 4,355,113 (1982), all issued to F. C. Mennen, disclose several devices containing TMP or DMP as the oxidase reagent for presumptive identification of N. gonorrhoeae in urethral exudates. A three-minute non-culture method for presumptive identification of N. gonorrhoeae in urethral exudates from men with urethral discharge was reported [Janda W. M., and T. Jackson, J. Clin. Microbiol. 21: 143-145 (1985)]. This method used a device containing TMP as the oxidase reagent to detect the cytochrome c oxidase systems (presumably those of the infecting gonococci in urethral exudates). This test had a sensitivity of 95.6% and a specificity of 84.2% for identification of N. gonorrhoeae in urethral exudates compared with the culture method; and the same results showed no significant difference compared with the Gram stain method. In a community, if the incidence of PPNG infection is high, the routine use of penicillin cannot be recommended for primary therapy unless penicillinase production in urethral specimens can first be excluded by a rapid screen test. A fluorescent spot test method [Chen, K. C. S., and K. K. Holmes, J. Clin. Microbiol. 23: 539-544 (1986)] was applied to the rapid and direct detection of PPNG in male urethral exudates [Taylor, D. N. et al., Lancet ii: 625-626 (1985)]. This method requires a long-wave ultraviolet lamp and a dark chamber for viewing the fluorescent end products. There are no methods for simultaneously detecting cytochrome c oxidase and penicillinase in urethral exudates for presumptive identification of *N. gonorrhoeae* and differentiation of the infecting gonococci into PPNG and non-PPNG.

Enzyme labels are required for an enzyme immunoassay (EIA) and a non-radioisotope DNA probe. The enzymes commonly used as labels are: horseradish peroxidase (HRP), glucose oxidase, alkaline phosphatase, beta-galactosidase, and urease. Recently, penicillinase was also used as an enzyme label for EIA [Yolken, R. H. et al., J. Immunol. Methods 73: 109–123 (1984)]. A simultaneous colorimetric assay method for any pair of the enzymes described above is currently not available, because the color signals produced by the two enzymes interfere with each other. Therefore, using current EIA or non-radioisotope DNA probe methods, two analytes in a specimen cannot be determined simultaneously.

This invention discloses a novel colorimetric assay for the open beta-lactam ring end product resulting from the hydrolysis of a beta-lactam substrate. It is an object of the present invention to provide a specific colorimetric assay for beta-lactamase including detection of microbial beta-lactamases. The chromophores used for beta-lactamase assay do not inactivate the beta-lactamase; therefore the assay method disclosed in this invention can be generally applied.

It is also an object of the present invention to provide a method for simultaneous detection of microbial cytochrome c oxidase systems and penicillinases to save time and decrease the number of organisms needed from culture for performing these two biochemical tests.

Further, it is an object of the present invention to provide a rapid nonculture method for simultaneous presumptive identification of *N. gonorrhoeae* in urethral exudates and differentiation of the infecting gonococci into PPNG and non-PPNG to facilitate the initial treatment for gonorrhea.

Another object of the present invention is to provide a colorimetric method for simultaneous assay for peroxidase and penicillinase using the same wavelength. Therefore, it provides great potential for analyzing two analytes in an incubation mixture using methods of EIA and non-radioisotope DNA probe with double enzyme labels.

Further objects and advantages will become apparent from consideration of the ensuing examples.

SUMMARY OF THE INVENTION

The present invention comprises a novel colorimetric method for beta-lactamase assay and its applications. The applications of this colorimetric method for beta-lactamase assay include a specific method for detection of microbial beta-lactamases; a method for simultaneous detection of microbial cytochrome c oxidase systems and penicillinases, and its application to simultaneous presumptive identification of *N. gonorrhoeae* in urethral exudates from men with urethral discharge, and differentiation of the infecting gonococci into PPNG and non-PPNG; and a simultaneous assay method for peroxidase and penicillinase.

The novel colorimetric method relies on the discovery that a chromophore solution formed by oxidation of TMP, DMP, or 3,3′,5,5′-tetramethylbenzidine (TMB) can be decolorized by the end product resulting from the hydrolysis of a cephalosporin by either beta-lactamase or alkali, but not by the intact cephalosporin. The same chromophore solution can be decolorized by the end product resulting from the hydrolysis of a penicillin by either beta-lactamase or alkali, only in the presence of an organomercury compound or an inorganic mercuric compound, but not by the intact penicillin.

In this invention, the chromophores formed by oxidation of the chromogenic substrates of peroxidase described above are referred to as the peroxidase-chromophores. This novel colorimetric method, based on decolorization of the peroxidase-chromophore by the open beta-lactam ring end product resulting from the hydrolysis of a beta-lactam antibiotic, is referred to as the peroxidase-chromophore decolorization method. Decolorization of a peroxidase-chromophore by an open beta-lactam ring end product resulting from the hydrolysis of a cephalosporin can be enhanced in the presence of organomercury compounds or inorganic mercuric compounds. Therefore, these mercury-containing compounds are referred to as the decolorization enhancers in this invention.

The peroxidase-chromophores discovered for use in the peroxidase-chromophore decolorization method described in this invention include the chromophores resulting from oxidation of substantially colorless chromogenic substrates of peroxidase, such as the 3,3′,5,5′-tetraalkyl derivative of benzidine, TMB and the N-alkyl derivative of p-phenylenediamine, DMP or TMP. DMP and TMP have also been used as oxidase reagents as described above.

Since the amount of an open beta-lactam ring end product produced enzymatically in a reaction mixture relates to the beta-lactamase activity, the peroxidase-chromophore decolorization method described in this invention provides a colorimetric method for qualitative or quantitative assay of beta-lactamase.

In addition to beta-lactamases, acylases that hydrolyze a beta-lactam antibiotic to form an acyl side-chain acid and a beta-lactam nucleus, are also commonly produced in microorganisms [Chen, K. C. S., Antimicrob. Agents Chemother. 30: 536–54 (1986)]. The intact beta-lactam nuclei such as, 6-aminopenicillanic acid (6-APA), 7-aminocephalosporanic acid (7-ACA), and 7-aminodesacetoxycephalosporanic acid (7-ADCA), and the acyl side-chain acids of some common beta-lactamase substrates do not decolorize the peroxidase-chromophores with or without the use of a decolorization enhancer. Therefore, the peroxidase-chromophore decolorization method described in this invention can differentiate beta-lactamase activity from acylase activity.

Decolorization of a peroxidase-chromophore by an open beta-lactam ring end product resulting from the hydrolysis of a penicillin can only occur in the presence of a decolorization enhancer. This allows simultaneous assay of penicillinase and peroxidase or cytochrome c oxidase, since the chromophore produced by either peroxidase or cytochrome c oxidase is not decolorized by the end product resulting from penicillinase activity prior to the addition of the decolorization enhancer.

The method for simultaneous detection of microbial cytochrome c oxidase systems and penicillinases can be applied to simultaneous presumptive identification of *N. gonorrhoeae* in urethral exudates from men with urethral discharge, and differentiation of the infecting gonococci into PPNG and non-PPNG without culture.

BRIEF DESCRIPTION OF THE DRAWINGS

FIG. 4 is a summary of the procedure for simultaneous detection of microbial cytochrome c oxidase systems and penicillinases using the peroxidase-chromophore decolorization method.

FIG. 5 is a summary of the procedure for simultaneous presumptive identification of *Neisseria gonorrhoeae* in urethral exudates, and differentiation of the infecting gonococci into penicillinase-producing *N. gonorrhoeae* (PPNG) and non-penicillinase-producing *N. gonorrhoeae* (non-PPNG) using the peroxidase-chromophore decolorization method.

FIG. 6 is a summary of the procedure for simultaneous assay of peroxidase and penicillinase using the peroxidase-chromophore decolorization method.

DETAILED DESCRIPTION OF THE INVENTION

Figure 1:
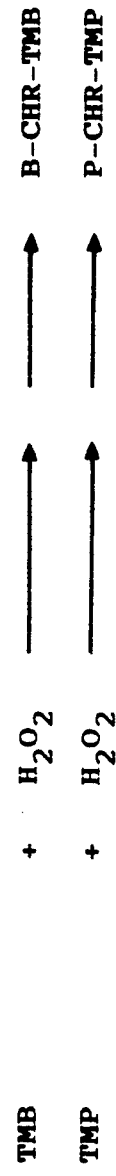
FIG. 1 is a summary of the procedure for preparing the peroxidase-chromophores.

This invention provides a novel colorimetric method for qualitative or quantitative determination of the end product resulting from the hydrolysis of a beta-lactam antibiotic by either beta-lactamase or alkali using the peroxidase-chromophore decolorization method. The peroxidase-chromophores, which can be decolorized by the open beta-lactam ring end products, but not by intact beta-lactam antibiotics, include: the pink chromophore from oxidized DMP (P-CHR-DMP); the purple chromophore from oxidized TMP (P-CHR-TMP); and the blue chromophore from oxidized TMB (B-CHR-TMB). The oxidation of DMP, TMP or TMB is preferably carried out by the HRP/$H_2O_2$ system, and the resulting chromophore is stabilized by adding catalase. A summary of the procedure for preparing the peroxidase-chromophores is shown in FIG. 1.

The decolorization enhancers are selected from a group of organomercury compounds with the common formula —C—Hg—A, and a group of inorganic mercuric compounds. The organomercury compounds, in which the carbon-mercury bond can be formed between mercury and a carbon in an aliphatic chain, an aromatic ring or a heterocyclic ring, consist of a wide range of structural types [Larock, R. C., "Organomercury Compounds in Organic Synthesis"; Reactivity and Structure Concepts in Organic Chemistry, 22: 4–154 (1985), Springer-Verlag Berlin Heidelberg New York Tokyo, K. Hafner, J.-M. Lehn, C. W. Rees, P. von R. Schleyer, B. M. Trost, and R. Zahradnik (eds.)]. The organomercury compounds used in this invention have a common formula, —C—Hg—A, in which Hg is concomitantly bonded to a carbon and to an anion. They include ethylmercuric chloride (EMC), mersalyl acid, thimerosal, p-aminophenylmercuric acetate (pAPMA), p-chloromercuribenzoic acid (pCMB), sodium p-chloromercuriphenylsulfonate (pCMPS), sodium p-hydroxymercuribenzoate (pHMB), sodium 2-(hydroxymercuri)benzoate (2HMB), sodium p-hydroxymercuriphenylsulfonate (pHMPS), phenylmercuric acetate (PMA), and sodium 5-mercuri-2'-deoxyuridine 5'-triphosphate (HgdUTP). The inorganic mercuric compounds used in this invention include mercuric acetate, mercuric bromide, mercuric chloride, mercuric nitrate, mercuric sulfate, and mercuric thiocyanate.

A peroxidase-chromophore can only be decolorized by the end product resulting from the hydrolysis of a penicillin by either beta-lactamase or alkali in the presence of a decolorization enhancer. The same peroxidase-chromophore can be decolorized by the end product resulting from the hydrolysis of a cephalosporin by either beta-lactamase or alkali in the absence of a decolorization enhancer, although the extent of decolorization can be increased in the presence of a decolorization enhancer.

Figure 2:
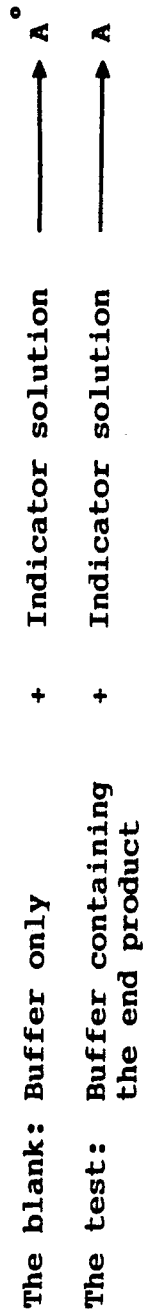
FIG. 2 is a summary of the procedure for assaying the open beta-lactam ring end product resulting from the hydrolysis of a beta-lactam antibiotic by either beta-lactamase or alkali using the peroxidase-chromophore decolorization method.

Qualitative or quantitative analysis of the open beta-lactam ring end product resulting from hydrolysis of a beta-lactam antibiotic by either beta-lactamase or alkali may be initiated by: (a) incubating aliquots of an indicator solution consisting of a peroxidase-chromophore such as B-CHR-TMB, P-CHR-TMP or P-CHR-DMP, and a decolorization enhancer such as pHMPS separately, with a buffer as the blank, and with the same volume of the buffer containing an open beta-lactam ring end product as the test; (b) determining the decolorization of the chromophore by the end product, qualitatively by comparing the color intensity of the blank with that of the test, or quantitatively by measuring the difference in absorbance between the blank and the test with a colorimeter. A summary of this procedure is shown in FIG. 2.

Figure 3:
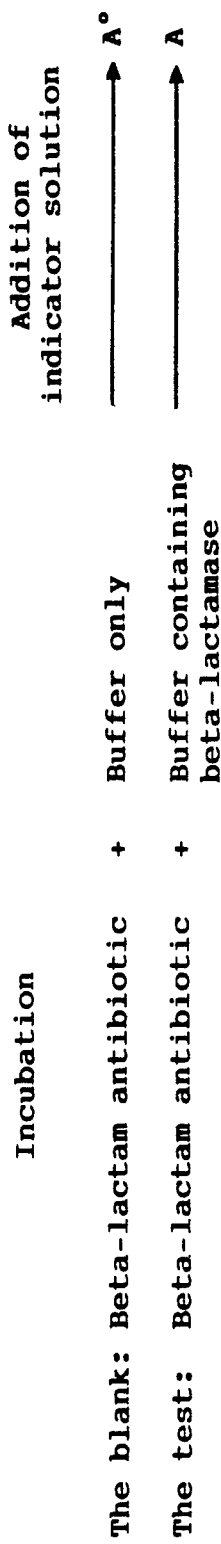
FIG. 3 is a summary of the procedure for assaying beta-lactamase using the peroxidase-chromophore decolorization method.

The amount of an open beta-lactam ring end product produced enzymatically in a reaction mixture is related to the beta-lactamase activity. Therefore, the beta-lactamase assay may be initiated as follows. (a) Aliquots of a beta-lactam substrate solution are incubated separately with a buffer as the blank, and with the same volume of the buffer containing a test microorganism thought to produce beta-lactamase or a cell-free beta-lactamase preparation as the test. (b) Aliquots of an indicator solution consisting of a peroxidase-chromophore such as B-CHR-TMB, P-CHR-TMP or P-CHR-DMP and a decolorization enhancer such as pHMPS, are added separately to the blank and to the test. (c) The decolorization of the chromophore by the enzymatically produced end product, is determined qualitatively by comparing the color intensity of the blank with that of the test, or quantitatively by measuring the difference in absorbance between the blank and the test with a colorimeter. A summary of this procedure is shown in FIG. 3.

Acylases which hydrolyze a beta-lactam antibiotic to form an acyl side-chain acid and a beta-lactam nucleus such as 6-APA, 7-ACA or 7-ADCA are commonly produced in microorganisms. The intact beta-lactam nuclei such as 6-APA, 7-ACA and 7-ADCA; and some commercially available acyl side-chain acids such as D(−)-α-aminophenylacetic acid (the common acyl side-chain acid of ampicillin, cephaloglycin and cephalexin), D(−)-p-hydroxyphenylglycine (the common acyl side-chain acid of amoxicillin and cefadroxil), phenylacetic acid (the acyl side-chain acid of penicillin G), phenoxyacetic acid (the acyl side-chain acid of penicillin V), and D-α-aminoadipic acid (the acyl side-chain acid of cephalosporin C), cannot decolorize the peroxidase-chromophores with or without the use of a decolorization enhancer. Therefore, the novel colorimetric assay method for beta-lactamase described in this invention can differentiate beta-lactamase activity from acylase activity if the aforementioned beta-lactam antibiotics are used as the substrates.

The peroxidase-chromophore decolorization method described in this invention can be used to assay penicillinase and peroxidase or cytochrome c oxidase simultaneously. This is possible because the chromophore produced by either cytochrome c oxidase or peroxidase cannot be decolorized by the end product resulting from penicillinase activity prior to the addition of a decolorization enhancer.

Consistent with these findings, simultaneous detection of microbial cytochrome c oxidase and penicillinase may be carried out as follows. (a) Aliquots of a combined substrate solution consisting of an oxidase reagent (TMP or DMP) and a penicillin are incubated separately with a buffer as the blank, and with the same volume of the buffer containing a test microorganism thought to produce cytochrome c oxidase and penicillinase simultaneously as the test. (b) The color intensity of the blank is compared with that of the test; an increase in color intensity of the test indicates cytochrome c oxidase activity, while a comparable color intensity between the blank and the test indicates the absence of cytochrome c oxidase activity. (c) To provide sufficient chromophore for the test solution incubated with oxidase-negative or weak oxidase-positive organisms, an appropriate amount of the corresponding catalase-stabilized peroxidase-chromophore (P-CHR-TMP or P-CHR-DMP) is added. (d) Aliquots of the test mixture with oxidase-positive organisms from (a) or with oxidase-negative or weak oxidase-positive organisms from (c) are incubated separately with a buffer as the blank and the same volume of the buffer containing a decolorization enhancer such as pHMPS as the test. (e) The color intensity of the blank is compared with that of the test; a decrease in color intensity or a complete decolorization of the test solution indicates penicillinase activity, while a comparable color intensity between the blank and the test indicates the absence of penicillinase activity. A summary of this procedure is shown in FIG. 4. Detection of penicillinase can also be carried out by visual estimation of the decolorization of the chromophore in (a) or (c) by placing a drop of the test mixture from (a) or (c) separately onto two pieces of filter paper. One piece is untreated and the other is impregnated with a decolorization enhancer such as pHMPS (soaked and dried). A comparable color intensity between the two spots indicates the absence of penicillinase activity, while a decrease in color intensity or a complete decolorization of the spot on the treated paper indicates penicillinase activity.

Using the method for simultaneous detection of microbial cytochrome c oxidase and penicillinase as described above, simultaneous presumptive identification of N. gonorrhoeae in urethral exudates from men with urethral discharge and differentiation of the infecting gonococci into PPNG and non-PPNG may be carried out as follows. (a) Aliquots of a combined substrate solution consisting of an oxidase reagent (TMP or DMP) and a penicillin, are incubated separately with a fresh swab as the blank and with a swab containing exudate as the test. (b) The color intensity of the blank is compared with that of the test. An increase in color intensity of the test indicates cytochrome c oxidase activity, which in turn indicates presumptive gonococcal infection; while a comparable color intensity between the blank and the test indicates the absence of cytochrome c oxidase activity, which in turn indicates presumptive non-gonococcal infection. (c) Aliquots of the test solution containing the oxidase-positive exudate are incubated separately with a buffer as the blank and with the same volume of the buffer containing a decolorization enhancer such as pHMPS as the test. (d) The color intensity of the blank is compared with that of the test. A comparable color intensity between the blank and the test indicates the absence of penicillinase activity, which in turn indicates presumptive non-PPNG infection; while a decrease in color intensity or a complete decolorization of the test indicates penicillinase activity, which in turn indicates presumptive PPNG infection. Detection of penicillinase activity in the exudate can also be carried out by visual estimation of the decolorization of the chromophore in the test with the oxidase-positive exudate as follows. A drop of the test mixture with the oxidase-positive exudate from (a) is placed separately onto two pieces of filter paper, one untreated and the other impregnated with a decolorization enhancer such as pHMPS (soaked and dried). Comparable color intensity between the two spots indicates the absence of penicillinase activity, which in turn indicates presumptive non-PPNG infection; while a decrease in color intensity or a complete decolorization of the spot on the treated paper indicates penicillinase activity, which in turn indicates presumptive PPNG infection. A summary of this procedure is shown in FIG. 5.

Using the peroxidase-chromophore decolorization method described in this invention, a simultaneous assay for peroxidase and penicillinase may be carried out as follows. (a) Aliquots of a combined substrate solution consisting of a peroxidase-chromogen plus $H_2O_2$ (TMB/$H_2O_2$, TMP/$H_2O_2$ or DMP/$H_2O_2$), and a penicillin, are incubated separately with a buffer as the blank and with the same volume of the buffer containing the combined enzymes as the test. (b) Peroxidase activity is assayed by quantitating the increase in absorbance of the test by measuring the absorbance of the test against the blank. (c) To provide sufficient chromophore for each assay mixture, aliquots of the peroxidase solution are separately added to both the blank and the test to convert the residual chromogen to chromophore. The mixtures are then stabilized separately by adding catalase. Alternatively, aliquots of the corresponding catalase-stabilized chromophore solution (B-CHR-TMB, P-CHR-TMP or P-CHR-DMP) are separately added to both the blank and the test. (d) The absorbance of the blank and that of the test are measured separately. (e) Aliquots of a decolorization enhancer solution are added separately to both the blank and the test, and their absorbances are measured separately again. (f) The concentrations of penicilloic acid in the blank and in the test are determined separately by computing the decrease in absorbance of the blank and that of the test before and after addition of the decolorization enhancer, after correction for dilution. Penicillinase activity is assayed by quantitating the enzymatically produced penicilloic acid by subtracting the concentration of penicilloic acid in the blank from that in the test. A summary of this procedure is shown in FIG. 6.

For decolorization of a peroxidase-chromophore by an open beta-lactam ring end product, the optimum concentration of a decolorization enhancer in the reaction mixture ranges from approximately 0.005 mM to approximately 3 mM; while the optimum time for decolorization reaction ranges from approximately 2 minutes to approximately 10 minutes at 20°–37° C. When organomercury compounds or inorganic mercuric compounds are used as the decolorization enhancers, sulhydryl-containing compounds in the reaction mixture may interfere with the assay. Therefore, concentrations of these mercury-containing compounds must be increased accordingly.

The stock solutions of TMP, DMP or TMB may be prepared by dissolving the free base form of TMP, DMP or TMB, or monohydrochloride form of DMP in N,N-dimethylformamide. The resulting solutions may be stored in a brown bottle at room temperature for months. Prior to use, an appropriate volume of buffer may be used to dilute each stock solution.

The following examples illustrate various aspects of the invention. However, it should be understood that the invention is not limited to the specific details of these examples.

EXAMPLE 1

A COLORIMETRIC METHOD FOR BETA-LACTAMASE ASSAY

MATERIALS

Chemicals

All chemicals and enzymes used in this invention were purchased from Sigma Chemical Co., St. Louis, Mo., with the exception of some organomercury compounds such as 2 HMB and EMC that were from K & K Laboratories, Div. of ICN Biomedicals, Inc., Cleveland, Ohio.

METHODS

Hydrolysis of the beta-lactam antibiotic by purified beta-lactamases

One milliliter of a 20 mM penicillin substrate in 50 mM sodium phosphate buffer, pH 6.7, was hydrolyzed with 5 μg of penicillinase (purified from *Bacillus cereus*), at 37° C. for 3 hours. One milliliter of a 20 mM cephalosporin substrate in the same buffer was hydrolyzed with 1 mg of cephalosporinase (purified from *Enterobacter cloacae*) and 5 μg of penicillinase (purified from *Bacillus cereus*, containing minor cephalosporinase activity), at 37° C. for 3 hours. Appropriate buffers were used to dilute each hydrolyzed mixture.

Hydrolysis of the beta-lactam antibiotic by alkali

Each 20 mM beta-lactam antibiotic in 0.33N NaOH was incubated at 25° C. for 10 minutes. The mixture was then neutralized with 1N HCl and appropriate buffers were used to dilute each hydrolyzed mixture.

Preparation of the stock solutions of the peroxidase-chromogens

The free base form of TMP, DMP or TMB and the monohydrochloride form of DMP were separately dissolved in N,N-dimethylformamide at a concentration of 100 mM and the resulting solutions were kept in a brown bottle at room temperature. Prior to use, each stock solution was diluted with water or appropriate buffers.

Preparation of the peroxidase-chromophores

Each substantially colorless peroxidase-chromogen was oxidized to form its appropriate chromophore by microbial cytochrome c oxidase system or the HRP/$H_2O_2$ system. TMP was oxidized to form a purple chromophore with maximum absorbance at a wavelength around 560 nm and 610 nm by gonococcal cytochrome c oxidase system. Similarly, it was oxidized to form a purple chromophore by the HRP/$H_2O_2$ system, but the absorbance of the purple chromophore decreases after prolonged incubation, or incubation in the excess of HRP. DMP was oxidized to form a pink chromophore with maximum absorbance at a wavelength around 510 nm and 550 nm by gonococcal cytochrome c oxidase system. Similarly, it was oxidized to form a pink chromophore by the HRP/$H_2O_2$ system, but the absorbance of the pink chromophore decreases after prolonged incubation, or incubation in the excess of HRP. TMB could only be oxidized by the HRP/$H_2O_2$ system to form a blue chromophore with a maximum absorbance at a wavelength around 650 nm. However, the blue chromophore turned green and eventually changed to yellow after prolonged incubation or incubation in the excess of HRP. The absorbance of the yellow chromophore at 650 nm is negligible when compared with that of the blue chromophore [Josephy, P. D. et al., J. Biol. Chem. 257: 3669–3675 (1982)]. If these chromophores are prepared by using the HRP/$H_2O_2$ system, they are stabilized by either catalase or sodium dodecyl sulfate. The blue chromophore from oxidized TMB (B-CHR-TMB), the purple chromophore from oxidized TMP (P-CHR-TMP), and the pink chromophore from oxidized DMP (P-CHR-DMP) can all be used as the chromophores for the peroxidase-chromophore decolorization method. However, P-CHR-DMP is the least sensitive and the least stable among the three chromophores employed. Therefore, P-CHR-DMP is not illustrated in the following examples. The solution of B-CHR-TMB was prepared as follows. An appropriate amount of HRP (e.g. 1 ng/ml) was added to a 0.1 mM TMB solution containing 1 mM $H_2O_2$ in 50 mM sodium phosphate buffer, pH 6.7; or in 50 mM sodium citrate buffer, pH 5.0. The reaction mixture was incubated at 20° C. until the absorbance of the reaction mixture at 650 nm approached its maximum. An appropriate amount of catalase (e.g. 20 μg/ml) was then added to stabilize the resulting chromophore. The solution of P-CHR-TMP was prepared similarly in either phosphate or citrate buffer, except that more HRP (e.g. 20 ng/ml) and more TMP (1 mM) were used for oxidation, the pH of the sodium citrate buffer was 6.0, and each reaction mixture was incubated at 25° C.

Preparation of the decolorization enhancer solutions

The organomercury compounds including pCMPS, pHMPS, HgdUTP and thimerosal, and the inorganic mercuric compounds including mercuric acetate, mercuric bromide, mercuric chloride, mercuric nitrate, mercuric sulfate and mercuric thiocyanate, are water soluble. An appropriate volume of buffer or deionized water was added to each compound to make the final concentration at 6 mM. The organomercury compounds including pAPMA, pCMB, EMC, pHMB, 2HMB, mersalyl acid, and PMA, are not readily water soluble. Their stock solutions were prepared as follows. An aqueous suspension of each compound was stirred with a magnetic stirrer while aliquots of 1N NaOH were added to the suspension. After the compound was dissolved, aliquots of 1 N HCl were added to the solution until it nearly turned cloudy, then an appropriate volume of buffer or deionized water was added to make the final concentration of each organomercury compound at 6 mM.

Decolorization of iodine-starch complex by hydrolyzed beta-lactam antibiotics

Two hundred microliters of an iodine-starch complex solution consisting of 0.24 mM $I_2$, 9.6 mM KI and 0.2% boiled starch in 50 mM sodium phosphate buffer, pH 6.7, was added to 100 μl of a 0.09 mM beta-lactam antibiotic (intact or hydrolyzed by either beta-lactamase or alkali) in the same buffer as the test. The reaction mixture was incubated at 30° C. for 20 minutes. A blank without the antibiotic, consisting of 200 μl of the iodine-starch complex solution and 100 μl of the phosphate buffer was incubated in the same manner. At the end of the incubation, 2.7 ml of deionized water was added separately to the test and the blank. Absorbance at 620 nm ($A_{620}$) of the diluted test and that of the diluted blank were measured separately against deionized water with a Spectronic 20. $A_{620}$ of the diluted blank was approximately 0.5 under the conditions described above. The percentage of decolorization of the reaction mixture containing the beta-lactam antibiotic (intact or hydrolyzed by either beta-lactamase or alkali) was determined as:

$$\left(1 - \frac{A_{620} \text{ of the diluted test}}{A_{620} \text{ of the diluted blank}}\right) \times 100$$

As listed in Table 1, 17 penicillins and 16 cephalosporins were separately hydrolyzed by either beta-lactamase or alkali, and all the resulting end products decolorized iodine-starch complex. As shown in Table 1, the contaminations of the hydrolyzed forms in the commercial sources may have caused certain penicillins such as azlocillin, carbenicillin, metampicillin, piperacillin, and ticarcillin to decolorize iodine-starch complex to some extent, since the microiodometric method is specific for detection of the open beta-lactam ring end products.

Decolorization of peroxidase-chromophores by hydrolyzed beta-lactam antibiotics with or without the use of a decolorization enhancer (A) Decolorization of P-CHR-TMP by hydrolyzed beta-lactam antibiotics:

The indicator solution (200 μl) consisting of 0.75 mM P-CHR-TMP and 1.5 mM pHMPS in 50 mM sodium phosphate buffer, pH 6.7, was added to 100 μl of a 3 mM beta-lactam antibiotic (intact or hydrolyzed by either beta-lactamase or alkali) in the same buffer as the test. The reaction mixture was incubated at 25° C. for 5 minutes. A blank without the antibiotic, consisting of 200 μl of the indicator solution and 100 μl of the phosphate buffer was incubated in the same manner. At the end of the incubation, 2.7 ml of deionized water was added separately to the test and the blank. $A_{610}$ of the diluted test and that of the diluted blank were measured separately against deionized water with a Spectronic 20. $A_{610}$ of the diluted blank under the conditions described above was approximately 0.5. The percentage of decolorization of the reaction mixture containing the antibiotic (intact or hydrolyzed by either beta-lactamase or alkali) was determined as:

$$\left(1 - \frac{A_{610} \text{ of the diluted test}}{A_{610} \text{ of the diluted blank}}\right) \times 100$$

The procedure for determining the percentage of decolorization of the reaction mixture containing a beta-lactam antibiotic (intact or hydrolyzed by either beta-lactamase or alkali) without the use of pHMPS were the same as that with the use of pHMPS as described above, except that pHMPS was absent in the indicator solution.

As shown in Table 2, the open beta-lactam ring end product resulting from hydrolysis of a penicillin by either beta-lactamase or alkali decolorized P-CHR-TMP only with the use of pHMPS; while that resulting from hydrolysis of a cephalosporin decolorized P-CHR-TMP with or without the use of pHMPS, although the extent of decolorization was greater when pHMPS was employed.

(B) Decolorization of B-CHR-TMB by hydrolyzed beta-lactam antibiotics:

The indicator solution (2.9 ml) consisting of 2.8 ml of a B-CHR-TMB in 50 mM sodium phosphate buffer, pH 6.7, with an $A_{650}$ approximately 0.5, and 0.1 ml of 6 mM pHMPS in the same buffer, was added to 100 μl of a 0.6 mM beta-lactam antibiotic (intact or hydrolyzed by either beta-lactamase or alkali) in the same buffer as the test. The reaction mixture was vortexed and incubated at 20° C. for 2 minutes. A blank without the antibiotic, which consisted of 2.9 ml of the indicator solution and 0.1 ml of the phosphate buffer was incubated in the same manner. $A_{650}$ of the test and that of the blank were measured separately against the phosphate buffer with a Spectronic 20. The percentage of decolorization of the reaction mixture containing a beta-lactam antibiotic (intact or hydrolyzed by either beta-lactamase or alkali) was determined as:

$$\left(1 - \frac{A_{650} \text{ of the test}}{A_{650} \text{ of the blank}}\right) \times 100$$

The procedure for determining the percentage of decolorization of the reaction mixture containing a beta-lactam antibiotic (intact or hydrolyzed by either beta-lactamase or alkali), without the use of pHMPS was the same as that with the use of pHMPS as described above, except that pHMPS was absent in the indicator solution.

As shown in Table 3, the open beta-lactam ring end product resulting from the hydrolysis of a penicillin decolorized B-CHR-TMB only with the use of pHMPS; while that resulting from the hydrolysis of a cephalosporin decolorized B-CHR-TMB with or without the use of pHMPS, although the extent of decolorization was greater when pHMPS was employed.

Specificity of the peroxidase-chromophore decolorization method for detection of the open beta-lactam ring end product resulting from the hydrolysis of a beta-lactam antibiotic by either beta-lactamase or alkali As shown in Table 4, most of the beta-lactam antibiotics foam commercial sources were unable to decolorize P-CHR-TMP or B-CHR-TMB, with the use of pHMPS. However, certain beta-lactam antibiotics that decolorized iodine-starch complex to some extent (Table 1) also decolorized P-CHR-TMP or B-CHR-TMB to a similar extent with the use of pHMPS. This was most likely due to contaminations of the hydrolyzed forms in the commercial sources. None of the penicillins from commercial sources decolorized P-CHR-TMP or B-CHR-TMB without the use of pHMPS, while the cephalosporins from commercial sources decolorized P-CHR-TMP or B-CHR-TMB to similar extent, with or without the use of pHMPS (results without the use of pHMPS not shown). Therefore, the peroxidase-chromophore decolorization method described in this invention is specific for detection of the open beta-lactam ring end product resulting from the hydrolysis of a beta-lactam antibiotic by either beta-lactamase or alkali.

Microbial acylases hydrolyze a beta-lactam antibiotic to form an acyl side-chain acid and a beta-lactam nucleus. As shown in Table 4, decolorization of P-CHR-TMP or B-CHR-TMB by the intact beta-lactam nucleus, such as 6-APA, 7-ACA or 7-ADCA, was negligible with or without the use of pHMPS (results without the use of pHMPS not shown). The acyl side-chain acids, such as D(−)-α-aminophenylacetic acid (the common acyl side-chain acid of ampicillin, cephaloglycin and cephalexin), D(−)-p-hydroxyphenylglycine (the common acyl side-chain acid of amoxicillin and cefadroxil), phenylacetic acid (the acyl side-chain acid of penicillin G), phenoxyacetic acid (the acyl side-chain acid of penicillin V), and D-α-aminoadipic acid (the acyl side-chain acid of cephalosporin C), prepared in the buffer at the concentration as described for the beta-lactam antibiotics listed in Table 4, failed to decolorize P-CHR-TMP or B-CHR-TMB, with or without the use of pHMPS (results not shown). Therefore, when the beta-lactam antibiotics with the acyl side-chain acids described above are used as substrates, the peroxidase-chromophore decolorization method described in this invention can distinguish beta-lactamase activity from acylase activity.

The open beta-lactam ring end products, the intact beta-lactam antibiotics including the intact beta-lactam nuclei, and some acyl side-chain acids had similar reactivities toward P-CHR-DMP as P-CHR-TMP and B-CHR-TMB described above (results not shown).

Quantitation of the open beta-lactam ring end product resulting from the hydrolysis of a beta-lactam antibiotic using the peroxidase-chromophore decolorization method Quantitation of the open beta-lactam ring end product resulting from the hydrolysis of a beta-lactam antibiotic by either beta-lactamase or alkali, using B-CHR-TMB as the chromophore was accomplished as follows. A volume (0.2 ml) of 3 mM pHMPS in 50 mM sodium citrate buffer, pH 5.0, was added to 2.8 ml of a solution of B-CHR-TMB in the citrate buffer, containing a given concentration of a hydrolyzed beta-lactam antibiotic as the test. The reaction mixture was vortexed and incubated at 20° C. for 2 minutes. A blank consisting of 2.8 ml of the same solution of B-CHR-TMB in the citrate buffer without the hydrolyzed beta-lactam antibiotic, and 0.2 ml of 3 mM pHMPS in the citrate buffer, was incubated in the same manner. At the end of the incubation, $A_{650}$ of the test and that of the blank were measured separately against the citrate buffer with a Spectronic 20. The decrease in $A_{650}$ of the test was calculated by subtracting $A_{650}$ of the test from that of the blank. The open beta-lactam ring end product resulting from the hydrolysis of a beta-lactam antibiotic by either beta-lactamase or alkali was quantitated by using the standard curve of the decrease in $A_{650}$ vs. the concentration of the open beta-lactam ring end product.

Figure 7:
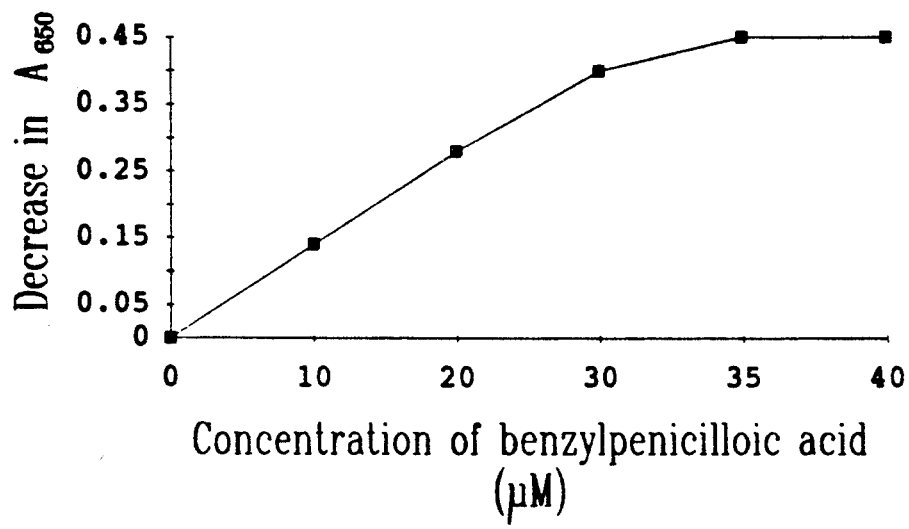
FIG. 7 is a graphical representation of the relationship between the decrease in absorbance at 650 nm ($A650$) of the catalase-stabilized blue chromophore solution prepared from oxidation of TMB, and the concentration of benzylpenicilloic acid.

FIG. 7 shows a standard curve of the decrease in $A_{650}$ vs. the concentration of benzylpenicilloic acid (the penicilloic acid of penicillin G). Each point represents the average of triplicate determinations.

Beta-lactamase assay using the peroxidase-chromophore decolorization method

Figure 8:
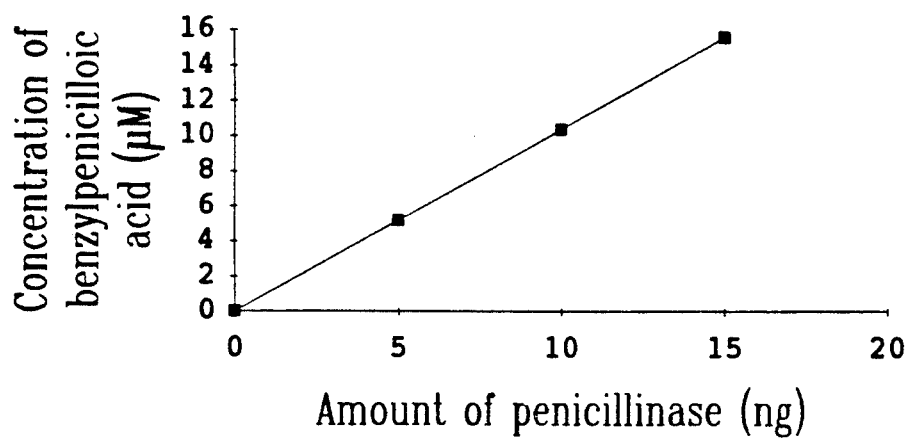
FIG. 8 is a graphical representation of the relationship between the concentration of benzylpenicilloic acid produced enzymatically and the amount of penicillinase in the assay mixture.

Use of B-CHR-TMB as the chromophore for beta-lactamase assay, using the peroxidase-chromophore decolorization method was accomplished as follows. A volume (2.8 ml) of a 0.6 mM penicillin (e.g. penicillin G) in a solution of B-CHR-TMB in 50 mM sodium citrate buffer, pH 5.0, containing penicillinase was incubated at 20° C. for 10 minutes as the test. A blank without the enzyme was incubated in the same manner. At the end of the incubation, 0.2 ml of 3 mM pHMPS in the citrate buffer was added separately to the test and the blank. Each reaction mixture was vortexed and further incubated at 20° C. for 2 minutes. $A_{650}$ of the test and that of the blank were measured separately against the citrate buffer with a Spectronic 20. The decrease in $A_{650}$ of the test was calculated by subtracting $A_{650}$ of the test from that of the blank. Penicillinase activity was determined by using two standard curves, the decrease in $A_{650}$ vs. the concentration of benzylpenicilloic acid as shown in FIG. 7, and the concentration of benzylpenicilloic acid vs. the amount of penicillinase as shown in FIG. 8 (penicillin G was used as the substrate). Each point in FIG. 8 represents the average of triplicate determinations.

Use of P-CHR-TMP as the chromophore for quantitating the open beta-lactam ring end product or beta-lactamase assay, using the peroxidase-chromophore decolorization method, can be accomplished similarly as described above for the use of B-CHR-TMB.

TABLE 1

Decolorization of iodine-starch complex by the intact or hydrolyzed beta-lactam antibiotics[a]

| beta-Lactam antibiotics | Percentage of decolorization of iodine-starch complex by the beta-lactam antibiotic (%) | | |
|---|---|---|---|
| | Intact | Hydrolyzed by beta-lactamase | alkali |
| Penicillins: | | | |
| 6-aminopenicillanic acid | 0 | 51 | 62 |
| amoxicillin | 2 | 80 | 72 |
| ampicillin | 0 | 90 | 86 |
| azlocillin | 9 | 78 | 78 |
| carbanicillin | 14 | 68 | 70 |
| cloxacillin | 0 | 34 | 84 |
| dicloxacillin | 0 | 18 | 76 |
| epicillin | 1 | 96 | 92 |
| hetacillin | 2 | 84 | 30 |
| metampicillin | 11 | 80 | 80 |

TABLE 1-continued

Decolorization of iodine-starch complex by the intact or hydrolyzed beta-lactam antibiotics[a]

| beta-Lactam antibiotics | Percentage of decolorization of iodine-starch complex by the beta-lactam antibiotic (%) | | |
|---|---|---|---|
| | Intact | Hydrolyzed by beta-lactamase | Hydrolyzed by alkali |
| methicillin | 0 | 74 | 78 |
| nafcillin | 0 | 26 | 84 |
| oxacillin | 0 | 82 | 80 |
| penicillin G | 0 | 82 | 76 |
| penicillin V | 0 | 92 | 94 |
| piparacillin | 18 | 60 | 64 |
| ticarcillin | 13 | 78 | 72 |
| Cephalosporins: | | | |
| 7-aminocephalosporanic acid | 2 | 6 | 36 |
| 7-aminodesaceoxy-cephalosporanic acid | 0 | 2 | 26 |
| cefaclor | 3 | 4 | 24 |
| cefadroxil | 2 | 46 | 56 |
| cefotaxime | 4 | 18 | 6 |
| cefoxitin | 0 | 2 | 22 |
| cefsulodin | 0 | 22 | 26 |
| ceftriaxone | 0 | 46 | 12 |
| cefuroxime | 0 | 18 | 2 |
| cephalexin | 0 | 42 | 56 |
| cephaloglycin | 3 | 22 | 40 |
| cephaloridine | 0 | 24 | 26 |
| cephalosporin C | 3 | 24 | 32 |
| cephalothin | 0 | 22 | 32 |
| cehapirin | 0 | 24 | 36 |
| cephradine | 2 | 50 | 60 |

[a]Detailed procedures were described in the text.

TABLE 2

Decolorization of the purple chromophore from oxidized N,N,N',N'-tetramethyl-p-phenylenediamine by hydrolyzed beta-lactam antibiotics without or with the use of sodium p-hydroxymercuriphenylsulfonate[a]

| Beat-lactum antibiotics | Percentage of decolorization of the purple chromophore (%) | | | |
|---|---|---|---|---|
| | Without sodium p-hydroxy mer-curiphanylsulfonate Hydrolyzed by | | With sodium p-hydroxy mer-curiphenylsulfonate Hydrolyzed by | |
| | beta-lactamase | alkali | beta-lactamse | alkali |
| Penicillins: | | | | |
| 6-aminopenicillanic acid | 0 | 0 | 96 | 98 |
| amoxicillin | 0 | 0 | 89 | 88 |
| ampicillin | 0 | 0 | 92 | 90 |
| azlocillin | 0 | 0 | 89 | 87 |
| carbenicillin | 0 | 0 | 93 | 92 |
| cloxacillin | 0 | 0 | 93 | 96 |
| dicloxacillin | 0 | 0 | 93 | 96 |
| epicillin | 2 | 1 | 95 | 86 |
| hetacillin | 0 | 0 | 86 | 48 |
| metampicillin | 0 | 0 | 88 | 87 |
| methicillin | 0 | 0 | 82 | 84 |
| nafcillin | 3 | 0 | 91 | 94 |
| oxacillin | 0 | 0 | 93 | 96 |
| penicillin G | 0 | 0 | 86 | 90 |
| penicillin V | 0 | 0 | 78 | 90 |
| piperacillin | 0 | 0 | 79 | 92 |
| ticarcillin | 0 | 0 | 93 | 96 |
| Cephalosporins: | | | | |
| 7-aminocephalosporanic acid | 8 | 20 | 16 | 98 |
| 7-aminodexacetoxy-cephalosporanic acid | 3 | 15 | 13 | 85 |
| cefaclor | 35 | 44 | 40 | 64 |
| cefadroxil | 69 | 42 | 71 | 74 |
| cefotaxime | 6 | 9 | 35 | 14 |
| cefoxitin | 0 | 15 | 2 | 35 |
| cefsulodin | 12 | 15 | 28 | 30 |
| ceftriaxone | 6 | 7 | 24 | 12 |
| cefuroxime | 7 | 7 | 23 | 12 |
| cephalexin | 73 | 39 | 80 | 69 |
| cephaloglycin | 24 | 28 | 49 | 49 |
| cephaloridine | 18 | 14 | 31 | 29 |
| cephalosporin C | 18 | 19 | 31 | 29 |
| cephalothin | 18 | 17 | 31 | 35 |
| cephapirin | 12 | 19 | 31 | 33 |
| cephradine | 63 | 33 | 66 | 69 |

[a]Detailed procedures were described in the text.

TABLE 3

Decolorization of the blue chromophore from oxidized 3,3',5,5'-tetramethyl-benzidine by hydrolyzed beta-lactam antibiotics without or with the use of sodium p-hydroxymercuriphenylsulfonate[a]

| Beat-lactum antibiotics | Percentage of decolorization of the blue chromophore (%) | | | |
|---|---|---|---|---|
| | Without sodium p-hydroxy mer-curiphanylsulfonate Hydrolyzed by | | With sodium p-hydroxy mer-curiphenylsulfonate Hydrolyzed by | |
| | beta-lactamase | alkali | beta-lactamse | alkali |
| Penicillins: | | | | |
| 6-aminopenicillanic acid | 0 | 0 | 66 | 68 |
| amoxicillin | 0 | 0 | 85 | 91 |
| ampicillin | 0 | 0 | 98 | 96 |
| azlocillin | 0 | 0 | 57 | 64 |
| carbenicillin | 0 | 0 | 59 | 65 |
| cloxacillin | 0 | 0 | 64 | 96 |
| dicloxacillin | 0 | 0 | 38 | 96 |
| epicillin | 2 | 0 | 98 | 98 |
| hetacillin | 0 | 0 | 94 | 42 |
| metampicillin | 0 | 0 | 94 | 98 |
| methicillin | 0 | 0 | 72 | 79 |
| nafcillin | 2 | 0 | 83 | 92 |
| oxacillin | 0 | 0 | 87 | 90 |
| penicillin G | 0 | 0 | 64 | 66 |
| penicillin V | 0 | 0 | 91 | 92 |
| piperacillin | 0 | 0 | 55 | 64 |
| ticarcillin | 0 | 0 | 80 | 81 |
| Cehalosporins: | | | | |
| 7-aminocephalosporanic acid | 4 | 2 | 7 | 47 |
| 7-aminodesacetoxy-cephalosporanic acid | 3 | 0 | 2 | 17 |
| cefaclor | 9 | 23 | 33 | 68 |
| cefadroxil | 24 | 17 | 66 | 82 |
| cefotaxime | 6 | 5 | 19 | 15 |
| ceoxitin | 0 | 11 | 2 | 28 |
| cefsulodin | 10 | 13 | 22 | 29 |
| ceftriaxone | 13 | 8 | 20 | 14 |
| cefuroxime | 5 | 6 | 19 | 9 |
| cephalexin | 27 | 20 | 58 | 80 |
| cephaloglycin | 10 | 15 | 33 | 48 |
| cephaloridine | 13 | 10 | 22 | 27 |
| cephalosporin C | 11 | 10 | 23 | 26 |
| cephalothin | 14 | 11 | 25 | 34 |
| cepapirin | 10 | 15 | 27 | 36 |
| cephradine | 13 | 16 | 58 | 63 |

[a]Detailed procedures were described in the text.

TABLE 4

Decolorization of the peroxidase-chromophores by intact beta-lactam antibiotics with the use of sodium p-phydoxymercuriphenylsulphonate[a]

| | Percentage of decolorization of the peroxidase-chromophore (%) | |
|---|---|---|
| Beta-lactam antibiotics | Purple chromophore from oxidized N,N,N',N'-tetramethyl-p-phenylenediamine | Blue chromophore from oxidized 3,3',5,5'-tetramethyl-benzidine |
| Penicillins: | | |
| 6-aminopenicillanic acid | 2 | 2 |
| amoxicillin | 3 | 3 |
| ampicillin | 1 | 2 |
| azlocillin | 10 | 4 |
| carbenicillin | 16 | 11 |
| clxacillin | 0 | 0 |
| dicloxacillin | 1 | 0 |
| epicillin | 2 | 2 |
| hetacillin | 3 | 3 |
| metampicillin | 14 | 13 |
| methicillin | 1 | 0 |
| nafcillin | 0 | 0 |
| oxacillin | 0 | 0 |
| penicillin G | 0 | 0 |
| penicillin V | 0 | 0 |
| piperacillin | 16 | 9 |
| ticarcillin | 14 | 10 |
| Cephalosporins: | | |
| 7-aminocephalo-spanic acid | 3 | 2 |
| 7-aminodesacetoxy-cephalosporanic acid | 0 | 0 |
| cefaclor | 4 | 4 |
| cefadroxil | 3 | 4 |
| cefotaxime | 4 | 2 |
| cefoxitin | 0 | 0 |
| cefsulodin | 0 | 0 |
| ceftriaxone | 0 | 0 |
| cefurpxime | 0 | 0 |
| cephalexin | 2 | 2 |
| cephaloglycin | 4 | 5 |
| cephaloridine | 0 | 0 |
| cephalosporin C | 3 | 2 |
| cephalothin | 0 | 0 |
| cepapirin | 0 | 0 |
| cephradine | 3 | 3 |

[a]Detailed procedures were described in the text.

EXAMPLE 2

DETECTION OF MICROBIAL BETA-LACTAMASES

The microorganisms and the growth conditions for each microorganism were described previously [Chen, K. C. S. et al., J. Clin. Microbiol. 19: 818–825 (1984)]. For each microorganism tested, a 200 μl-volume of a 1.5 mM penicillin or cephalosporin substrate in 50 mM sodium phosphate buffer, pH 6.7, was separately dispensed into two tubes, one containing 50 μl of phosphate-buffered saline (PBS: 0.15 M NaCl in 50 mM sodium phosphate buffer, pH 6.7) as the blank and the other as the test containing 50 μl of a bacterial suspension in PBS, consisting of approximately a loopful (diameter: 2 mm) of growth of each strain removed from the agar plate. Both tubes were incubated at 37° C. for 15 minutes, then a 50 μl-volume of indicator solution, consisting of 0.75 mM P-CHR-TMP and 6 mM pHMPS in the phosphate buffer was added separately to both tubes. The mixtures were further incubated for 3 minutes at 37° C. At the end of the incubation, the color intensity of the blank was compared with that of the test. A comparable color intensity between the two tubes indicated a negative test for the beta-lactamase activity; while a decrease in color intensity or a complete decolorization of the test indicated a positive test for the beta-lactamase activity in the organism.

Table 5 lists activities of penicillinase (ampicillin as the substrate) and cephalosporinase (cephalexin as the substrate) in the selected microorganisms, determined by both the peroxidase-chromophore decolorization method described in this invention and the fluorescent spot test method described previously [Chen, K. C. S., and K. K. Holmes, J. Clin. Microbiol. 23: 539–544 (1986)]. The results from both methods agreed completely.

TABLE 5

Activities of beta-lactamases in selected microorganisms determined by the peroxidase-chromophore decolorization method and the fluorescence method[a]

| | Peroxidase-chromophore decolorization method | | Fluorescence method | |
|---|---|---|---|---|
| Microorganisms | Penicillinase | Cephalosporinase | Penicillinase | Cephalosporinase |
| Gram-negative bacteria: | | | | |
| Eikenella corrodens ATCC 23834 | − | − | − | − |
| Enterobacter aerogenes ATCC 13048 | − | + | − | + |
| Enterobacter agglomerans ATCC 29915 | + | − | + | − |
| Enterobacter cloacae ATCC 13047 | − | + | − | + |
| Klebsiella pnenoniae ATCC 13883 | + | − | + | − |
| Neisseria gonorrhoeae | | | | |
| TVD 1,2 | − | − | − | − |
| TVD 3,4 | + | + | + | + |
| Providencia rettgeri ATCC 9250, 31052 | − | − | − | − |
| Pseudomonas aeruginosa ATCC 17434, 27853 | − | − | − | − |
| Pseudomonas putida ATCC 25571 | − | + | − | + |
| Gram-positive bacteria: | | | | |
| Bacillus cereus ATCC 13061, 27348 | + | − | + | − |
| Staphylococcus aureus ATCC 12598, 25923 | − | − | − | − |
| Enterococcus faecalis ATCC 11420, 12984 | − | − | − | − |

[a]Detailed procedures were described in the text.

EXAMPLE 3

SIMULTANEOUS DETECTION OF MICROBIAL CYTOCHROME C OXIDASE SYSTEMS AND PENICILLINASE

Selection of substrate for penicillinase

Some clinically important microorganisms such as Heamophilus influenzae, Neisseria gonorrhoeae and Pseudomonas aeruginosa produce cytochrome c oxidase. Among these oxidase-positive organisms, some also produce penicillinase. To select a penicillinase substrate for simultaneous detection of cytochrome c oxidase system and penicillinase in a strain of penicillinase-producing N. gonorrhoeae (PPNG), a 100 μl-volume of the PBS-suspension of a strain of PPNG containing approximately two loopfuls (diameter: 2 mm) of growth removed from the agar plate, was added separately to a 400 μl-volume of a combined substrate solution, consisting of 0.75 mM TMP and a 1.5 mM penicillin substrate in 50 mM sodium phosphate buffer, pH 6.7. Each reaction mixture was incubated at 37° C. for 10 minutes. Half of the reaction mixture was added to a tube containing 50 μl of the phosphate buffer as the blank and the other half was added to a tube containing 50 μl of 6 mM pHMPS in the same buffer as the test. Each reaction mixture was further incubated at 37° C. for 3 minutes and 2.7 ml of deionized water was added to each tube. $A610$ of the diluted test and that of the diluted blank were measured separately against deionized water with a Spectronic 20. As shown in Table 6, after incubation, TMP was oxidized to its maximum color intensity by gonococcal cytochrome system; while the penicillin substrates were hydrolyzed to different extents by gonococcal penicillinase. Table 6 shows suitable penicillin substrates for determining penicillinase activity in PPNG such as: 6-aminopenicillanic acid, ampicillin, epicillin, hetacillin, penicillin G and penicillin V. Although carbenicillin and piperacillin were also hydrolyzed to a great extent, they were not suitable substrates due to the contaminations of the hydrolyzed forms in the commercial sources, as shown in Table 4.

Simultaneous detection of microbial cytochrome c oxidase systems and penicillinases For simultaneous detection of microbial cytochrome c oxidase systems and penicillinases, a 200 μl-volume of the combined substrate solution, consisting of 0.75 mM TMP and 1.5 mM ampicillin in 50 mM sodium phosphate buffer, pH 6.7, was dispensed separately into two tubes. One tube contained 50 μl of PBS as the blank, and the other contained 50 μl of the bacterial PBS-suspension, consisting of approximately a loopful (diameter: 2 mm) of growth of each strain removed from the agar plate as the test. Each mixture was incubated at 37° C. for 15 minutes and the color intensity of the blank was compared with that of the test. An increase in color intensity of the test indicated the presence of cytochrome c oxidase system in the organism; while a comparable color intensity between the blank and the test indicated the absence of cytochrome c oxidase system in the organism. If cytochrome c oxidase system was found to be present in the organism, an 8 μl-volume of the test was spotted separately on two pieces of Whatman 3 MM paper. One was untreated and the other was impregnated with 1 mM pHMPS in 50 mM sodium phosphate buffer, pH 6.7, (soaked and dried). The color intensities of these two spots were compared three minutes after their applications. A comparable color intensity between the two spots indicated the absence of penicillinase activity; while a decrease in the color intensity or a complete decolorization of the spot on the pHMPS-impregnated paper indicated the presence of penicillinase activity. If the organism was found to be negative or weak for cytochrome c oxidase system, 50 μl of 1 mM P-CHR-TMP was added to the test to provide enough chromophore for the reaction mixture, and detection of penicillinase was proceeded as described above for the oxidase-positive organisms. Table 7 shows the activities of cytochrome c oxidase and penicillinase in the microorganisms as listed in Table 5.

TABLE 6

Absorbance of the diluted reaction mixture at 610 nm after incubation of a strain of penicillinase-producing *N. gonorrhoeae* with each combined substrate solution containing N,N,N',N'-tetramethyl-p-phenylenediamine and a penicillin without or with addition of sodium p-hydroxymercuriphenylsulfonate[a]

| Penicillins | Treatment of reaction mixture after incubation | |
|---|---|---|
| | Without sodium p-hydroxy-mercuriphenylsulfonate | With sodium p-hydroxymercuriphenylsulfonate |
| 6-aminopenicillanic acid | 0.49 | 0.07 |
| amoxicillin | 0.49 | 0.25 |
| ampicillin | 0.49 | 0.17 |
| azlocillin | 0.50 | 0.27 |
| carbanicillin | 0.47 | 0.23 |
| cloxacillin | 0.49 | 0.45 |
| dicloxacillin | 0.49 | 0.47 |
| epicillin | 0.49 | 0.19 |
| hetacillin | 0.49 | 0.20 |
| metazpicillin | 0.50 | 0.39 |
| methicillin | 0.49 | 0.46 |
| nafcillin | 0.49 | 0.46 |
| oxacillin | 0.49 | 0.46 |
| penicillin G | 0.49 | 0.18 |
| penicillin V | 0.49 | 0.20 |
| piperacillin | 0.47 | 0.17 |
| ticarcillin | 0.48 | 0.29 |

[a]Detailed procedures were described in the text.

TABLE 7

Simultaneous detection of activities of cytochrome c oxidase and penicillinase in selected microorganisms by the peroxidase-chromophore and ampicillin as the combined substrates[a]

| Microorganisms | Cytochrome c oxidase | penicillinase |
|---|---|---|
| Gram-negative bacteria: | | |
| Eikenella corrodens ATCC 23834 | + | − |
| Enterobacter aerogenes ATCC 13048 | − | − |
| Enterobacter agglomerans ATCC 29915 | − | + |
| Enterobacter cloacae ATCC 13047 | − | − |
| Klebsiella pnenoniae ATCC 13883 | − | + |
| Neisseria gonorrhoeae | | |
| TVD 1,2 | + | − |
| TVD 3,4 | + | + |
| Providencia rettgeri ATCC 9250, 31052 | − | − |
| Pseudomonas aeruginosa ATCC 17434, 27853 | + | − |
| Pseudomonas putida ATCC 25571 | + | − |
| Gram-positive bacteria: | | |
| Bacillus cereus ATCC 13061, 27348 | + | + |
| Staphylococcus aureus ATCC 12598, 25923 | − | − |
| Enterococcus faecalis ATCC 11420, 12984 | − | − |

[a]Detailed procedures were described in the text.

EXAMPLE 4

SIMULTANEOUS PRESUMPTIVE IDENTIFICATION OF *Neisseria gonorrhoeae* IN URETHRAL EXUDATES FROM MEN WITH URETHRAL DISCHARGE AND DIFFERENTIATION OF THE INFECTING GONOCOCCI INTO PENICILLINASE-PRODUCING *Neisseria gonorrhoeae* AND NON-PENICILLINASE-PRODUCING *Neisseria gonorrhoeae*

An exudate specimen from the urethra was Gram stained and examined microscopically for intracellular Gram-negative diplococci in polymorphonuclear leucocytes. If the exudate had a positive Gram stained smear, urethral exudate specimens were further collected with two swabs. One swab was inoculated onto modified Thayer-Martin medium, and the inoculated medium was incubated at 37° C. for 24–72 hours in a $CO_2$-incubator. Subculture was performed if necessary. Presumptive gonococcal isolates were characterized by colony morphology, oxidase test and Gram stain. Penicillinase production was tested by the fluorescent spot test method described previously [K. C. S. Chen and K. K. Holmes J. Clin. Microbiol. 23:539-544 (1986)]. The other exudate-containing swab was placed into a microcentrifuge tube containing 100 µl of the combined substrate solution, consisting of 0.75 mM TMP and 1.5 mM ampicillin in 50 mM sodium phosphate buffer, pH 6.7, as the test. The tube was incubated for 10 minutes at 37° C. along with an uninoculated blank tube containing the same volume of the combined substrate solution with a fresh swab. At the end of the incubation, the color intensity of the test was compared with that of the blank. An increase in color intensity of the test was the indication of cytochrome c oxidase activity in the exudates, which in turn indicated a presumptive identification of *N. gonorrhoeae* in the exudate. If the cytochrome c oxidase test was positive, an approximately 8 µl-volume of the reaction mixture from the test was spotted separately on two pieces of Whatman 3 MM paper, one untreated and the other impregnated with 1 mM pHMPS in phosphate buffer (soaked and dried). Three minutes after the application, the color intensity of the spot on the untreated paper was compared with that on the treated paper. A comparable color intensity between the two spots indicated the absence of penicillinase activity, which in turn indicated a presumptive identification of non-PPNG in the exudate; while a decrease in color intensity or a complete decolorization of the spot on the pHMPS-impregnated paper indicated the presence of penicillinase activity in the exudate, which in turn indicated a presumptive identification of PPNG in the exudate.

Patients were included in the study on the basis of a positive Gram stained smear and a positive culture for *N. gonorrhoeae*. Among 44 exudate specimens positive for intracellular Gram-negative diplococci by Gram stain and *N. gonorrhoeae* by culture, 42 were positive for cytochrome c oxidase by this rapid test. Two were false-negatives. Among 42 gonococcal isolates cultured from the oxidase-positive exudates, 27 were positive for penicillinase using the fluorescent spot test method. Among those 27 culture-proven PPNG containing exudates, 26 were positive for penicillinase using this rapid test. One was a false-negative. No false-positive results for penicillinase activity were found among the oxidase-positive exudates by this rapid test method.

EXAMPLE 5

SIMULTANEOUS ASSAY METHOD FOR PEROXIDASE AND PENICILLINASE

Figure 9:
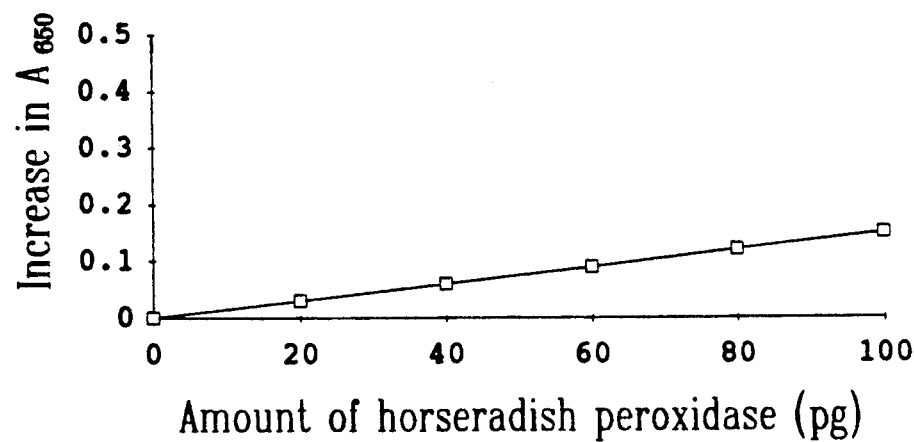
FIG. 9 is a graphical representation of the relationship between the increase in absorbance at 650 ($A650$) resulting from enzymatic oxidation of TMB and the amount of HRP in the simultaneous assay mixture using TMB and penicillin G as the combined substrates.
Figure 10:
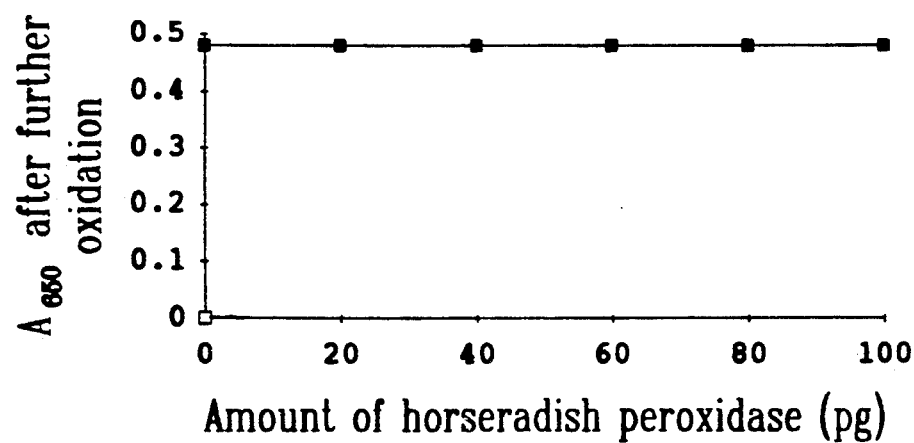
FIG. 10 is a graphical representation of the absorbance at 650 nm ($A650$) of each simultaneous assay mixture shown in FIG. 9 after further incubation for 3 minutes with an additional 5 ng of HRP.

The simultaneous assay for HRP and penicillinase using $TMB/H_2O_2$ and penicillin G as the combined substrates was as follows. A 0.1 ml-volume of a combined enzyme solution, consisting of a given amount of HRP and penicillinase in 50 mM sodium citrate buffer, pH 5.0, was added to 2.6 ml of the combined substrate solution which consisted of 0.06 mM TMB, 1 mM $H_2O_2$ and 0.6 mM penicillin G in the same citrate buffer. The test mixture was incubated at 20° C. for 10 minutes. A blank consisting of an equal volume of the combined substrate solution and 0.1 ml of citrate buffer, but no enzymes, was incubated in the same manner. At the end of the incubation, $A_{650}$ of the test was measured against the blank with a Spectronic 20. The amount of HRP in the assay mixture was then determined by quantitating the increase in $A_{650}$ of the test as shown in FIG. 9. For penicillinase assay, a 0.1 ml-volume of the exotic peroxidase solution, containing an appropriate amount of HRP (e.g. 5 ng), was separately added to each reaction mixture, including the blank. Each mixture was further incubated at 20° C. until $A_{650}$ of the blank reached near its maximum (e.g. further incubated for 5 minutes). Then, 0.1 ml of catalase suspension (1 mg/ml) was separately added to each mixture including the blank, to stabilize the chromophore. $A_{650}$ of each mixture including the blank was measured against the citrate buffer as shown in FIG. 10. For determination of the concentration of benzylpenicilloic acid in each assay mixture, a 0.1 ml-volume of 6 mM pHMPS in citrate buffer was added to each mixture including the blank. $A_{650}$ of each reaction mixture was measured against the citrate buffer after incubation at 20° C. for 2 minutes. The decrease in $A_{650}$ after addition of pHMPS was determined after correction for dilution. The concentration of benzylpenicilloic acid in each reaction mixture was determined as described in Example 1. The amount of penicillinase in the reaction mixture was determined by determining enzymatically produced benzylpenicilloic acid by subtracting the concentration of benzylpenicilloic acid in the blank from that in the test as described in Example 1.

VARIATIONS, SUMMARY, RAMIFICATIONS, AND SCOPE

Through reference to the above examples, variations on the disclosed methods will readily become apparent. Some examples are as follows. (a) In the preparation of the peroxidase-chromophores, HRP can be replaced by other peroxidases, such as lactoperoxidase or some peroxidatively active substances such as hemoglobin or myoglobin. $H_2O_2$ can be replaced by other peroxides such as urea hydrogen peroxide. (b) Using the $HRP/H_2O_2$ system to prepare the peroxidase-chromophores, the chromophores can also be stabilized by inhibiting HRP, such as by adding sodium dodecyl sulfate to the reaction mixture to a final concentration of 1 per cent. (c) The peroxidase-chromophores from the oxidase reagents, such as TMP and DMP, can be prepared by auto-oxidation of these chromogens in solution. (d) The decolorization enhancer used in a decolorization reaction can be prepared by mixing a suitable combination of the mercury-containing compounds. (e) For assaying beta-lactamase activity, the substrate can be prepared by mixing a suitable combination of the beta-lactam antibiotics if none of the substrates used are competitive inhibitors to the enzyme. (f) For assaying penicillinase activity, the substrate can be prepared by mixing a suitable combination of the penicillins if none of the substrates used are competitive inhibitors to the enzyme. (g) For assaying penicillinase activity, the peroxidase-chromophores described in this invention can be included in the penicillin substrate solution, since they do not inhibit beta-lactamase activity, and are not decolorized by the open beta-lactam ring end product prior to the addition of a decolorization enhancer.

To summarize, a novel beta-lactamase assay is proposed, using the peroxidase-chromophore decolorization method described in this invention, for qualitative or quantitative analysis of the open beta-lactam ring end product resulting from the hydrolysis of a beta-lactam antibiotic. A penicillinase assay using the peroxidase-chromophore decolorization method was coupled to that for cytochrome c oxidase or peroxidase, using the same chromophore for simultaneous assay of penicillinase and cytochrome c oxidase or peroxidase.

The result obtained using the procedures described in the above examples showed the following. (a) The peroxidase-chromophores could be easily prepared by oxidation of some chromogenic substrates of peroxidase such as TMP, DMP, and TMB. (b) The open beta-lactam ring end product resulting from the hydrolysis of a penicillin decolorized the peroxidase-chromophores in the presence of a decolorization enhancer which was a mercury-containing compound. The open beta-lactam ring end product resulting from the hydrolysis of a cephalosporin decolorized the peroxidase-chromophores with or without the use of a decolorization enhancer, although the extent of decolorization was greater when the decolorization enhancer was used. (c) The peroxidase-chromophore decolorization method was specific for detection of the open beta-lactam ring end products and could distinguish beta-lactamase activity from acylase activity. (d) The peroxidase-chromophore decolorization method could be used for detecting microbial beta-lactamases as well as for beta-lactamase assay. (e) The assay method for penicillinase, using the peroxidase-chromophore decolorization method, could be coupled to that of cytochrome c oxidase or peroxidase for the simultaneous assay of penicillinase and cytochrome c oxidase or peroxidase. (f) The simultaneous assay of penicillinase and cytochrome c oxidase could be applied to presumptive identification of *Neisseria gonorrhoeae* in urethral exudates from men with urethral discharge and to further differentiation of the infecting gonococci into penicillinase-producing *N. gonorrhoeae* and non-penicillinase-producing *N. gonorrhoeae*.

Although the description of the above examples contains many specificities, these should not be construed as limiting the scope of the invention but merely as providing illustrations of some of the presently preferred embodiments of this invention. For example, it is known that an assay for an oxidase such as glucose oxidase or cholesterol oxidase may be carried out by coupling a peroxidase to the assay system. In the oxidase assay, hydrogen peroxide generated by the oxidase activity serves as the substrate for the exotic peroxidase to oxidize a chromogenic substrate. Formation of the chromophore is the indication of oxidase activity. Therefore, a method for simultaneous assay of an oxidase and a penicillinase can be developed by coupling the penicillinase assay, using the peroxidase-chromophore decolorization method described in this invention, to the oxidase assay. For example, in the oxidase assay, hydrogen peroxide generated by the oxidase activity is used by a peroxidase to oxidize a chromogenic substrate such as TMB, TMP, or DMP to form a peroxidase-chromophore. Oxidase activity is determined by measuring the peroxidase-chromophore formed. Peroxide, such as hydrogen peroxide or the peroxidase-chromophore is then added to the reaction mixture to provide sufficient chromophore, and the penicillinase assay can be carried out as described for the simultaneous assay of peroxidase and penicillinase.

Thus the scope of the invention should be determined by the appended claims and their legal equivalents, rather than by the examples given.

I claim:

1. A beta-lactamase assay by qualitative or quantitative analysis of an open beta-lactam ring end product resulting from the hydrolysis of an amide bond in a beta-lactam ring of a beta-lactam antibiotic, catalyzed by a beta-lactamase, comprising:
   (a) incubating a beta-lactam antibiotic with either an organism thought to produce beta-lactamase, or a cell-free beta-lactamase preparation, to produce an incubated mixture;
   (b) bringing said incubated mixture into contact with an indicator solution consisting essentially of a chromophore, prepared by oxidation of either an N-alkyl derivative of p-phenylenediamine or a 3,3',5,5'-tetraalkyl derivative of benzidine, and a mercury-containing compound, to produce a reaction mixture; and
   (c) determining the beta-lactamase activity by measuring the decolorization of the chromophore in said reaction mixture, caused by the open beta-lactam ring end product resulting from beta-lactamase hydrolysis of said beta-lactam antibiotic.

2. The method of claim 1 wherein the N-alkyl derivative of p-phenylenediamine is selected from the group consisting of N,N,N',N'-tetramethyl-p-phenylenediamine and N,N-dimethyl-p-phenylenediamine, and the 3,3',5,5'-tetraalkyl derivative of benzidine is 3,3',5,5'-tetramethylbenzidine.

3. The method of claim 1 wherein the mercury-containing compound is either an inorganic mercuric compound, or an organomercury compound with the common formula, —C—Hg—A, in which Hg is concomitantly bonded to a carbon in an aliphatic chain, in an aromatic ring, or in a heterocyclic ring and to an anion.

4. The method of claim 3 wherein the inorganic mercuric compound is selected from a group consisting of mercuric acetate, mercuric bromide, mercuric chloride, mercuric nitrate, mercuric sulfate, and mercuric thiocyanate; while the organomercury compound is selected from a group consisting of ethylmercuric chloride, mersalyl acid, thimerosal, p-aminophenylmercuric acetate, p-chloromercuribenzoic acid, sodium p-chloromercuriphenylsulfonate, sodium p-hydroxymercuribenzoate, sodium 2-(hydroxymercuri)benzoate, sodium p-hydroxymercuriphenylsulfonate, phenylmercuric acetate, and sodium 5-mercuri-2'-deoxyuridine 5'-triphosphate.

5. The method of claim 1 wherein said reaction mixture contains the mercury-containing compound in a final concentration ranging from 0.005 mM to 3 mM and has a pH ranging from 3.5 to 8.0.

6. A cephalosporinase assay by qualitative or quantitative analysis of an open beta-lactam ring end product resulting from the hydrolysis of an amide bond in a beta-lactam ring of a cephalosporin, catalyzed by a cephalosporinase, comprising:
(a) incubating a cephalosporin with either an organism thought to produce cephalosporinase, or a cell-free cephalosporinase preparation, to produce an incubated mixture;
(b) bringing said incubated mixture into contact with a chromophore solution prepared by oxidation of either an N-alkyl derivative of p-phenylenediamine or a 3,3',5,5'-tetraalkyl derivative of benzidine, to produce a reaction mixture; and
(c) determining the cephalosporinase activity by measuring the decolorization of the chromophore in said reaction mixture, caused by the open beta-lactam ring end product resulting from cephalosporinase hydrolysis of said cephalosporin.

7. The method of claim 6 wherein the N-alkyl derivative of p-phenylenediamine is selected from the group consisting of N,N,N',N'-tetramethyl-p-phenylenediamine and N,N-dimethyl-p-phenylenediamine, and the 3,3',5,5'-tetraalkyl derivative of benzidine is 3,3',5,5'-tetramethylbenzidine.

8. The method of claim 6 wherein said reaction mixture has a pH ranging from 3.5 to 8.0.

9. A method for the simultaneous detection of a microbial cytochrome c oxidase system and a penicillinase by simultaneous detection of a chromophore resulting from oxidation of an oxidase reagent, catalyzed by the cytochrome c oxidase system and an open beta-lactam ring end product resulting from the hydrolysis of a penicillin, catalyzed by a penicillinase, comprising:
(a) incubating a combined substrate solution, consisting essentially of an N-alkyl derivative of p-phenylenediamine as the oxidase reagent, and a penicillin as the penicillinase substrate, with either an organism thought to produce a cytochrome c oxidase system and a penicillinase simultaneously, or a cell-free preparation thought to contain a cytochrome c oxidase system and a penicillinase, to produce an incubated mixture;
(b) detecting the cytochrome c oxidase system by detecting the chromophore in said incubated mixture resulting from the oxidation of said oxidase reagent, catalyzed by the cytochrome c oxidase system;
(c) supplementing said incubated mixture from step (a) with a sufficient amount of chromophore, prepared by oxidation of an oxidase reagent which is identical to the oxidase reagent used in step (a), if necessary;
(d) bringing the incubated mixture from step (a) or the supplemented incubated mixture from step (c) into contact with a mercury-containing compound, to produce a reaction mixture; and
(e) detecting the penicillinase activity by detecting the decolorization of the chromophore in said reaction mixture, caused by the open beta-lactam ring end product resulting from penicillinase hydrolysis of said penicillin.

10. The method of claim 9 wherein the N-alkyl derivative of p-phenylenediamine is selected from the group consisting of N,N,N',N'-tetramethyl-p-phenylenediamine, and N,N-dimethyl-p-phenylenediamine.

11. The method of claim 9 wherein the mercury-containing compound is either an inorganic mercuric compound, or an organomercury compound with the common formula, —C—Hg—A, in which Hg is concomitantly bonded to a carbon in an aliphatic chain, in an aromatic ring, or in a heterocyclic ring and to an anion.

12. The method of claim 11 wherein the inorganic mercuric compound is selected from a group consisting of mercuric acetate, mercuric bromide, mercuric chloride, mercuric nitrate, mercuric sulfate, and mercuric thiocyanate; while the organomercury compound is selected from a group consisting of ethylmercuric chloride, mersalyl acid, thimerosal, p-aminophenylmercuric acetate, p-chloromercuribenzoic acid, sodium p-chloromercuriphenylsulfonate, sodium p-hydroxymercuribenzoate, sodium 2-(hydroxymercuri)benzoate, sodium p-hydroxymercuriphenylsulfonate, phenylmercuric acetate, and sodium 5-mercuri-2'-deoxyuridine 5'-triphosphate.

13. The method of claim 9 wherein said reaction mixture contains the mercury-containing compound in a final concentration ranging from 0.005 mM to 3 mM, and has a pH ranging from 3.5 to 8.0.

14. A simultaneous assay method for peroxidase and penicillinase by simultaneous qualitative or quantitative analysis of a chromophore resulting from oxidation of a chromogenic substrate, catalyzed by a peroxidase, and an open beta-lactam ring end product resulting from the hydrolysis of a penicillin, catalyzed by a penicillinase, comprising:
(a) incubating a combined substrate solution, consisting essentially of a chromogenic substrate which is either an N-alkyl derivative of p-phenylenediamine or a 3,3',5,5'-tetraalkyl derivative of benzidine, and a peroxide as the peroxidase substrates, and a penicillin as the penicillinase substrate, with a combined enzyme solution thought to contain a peroxidase and a penicillinase, to produce an incubated mixture;
(b) determining the peroxidase activity by measuring the chromophore in said incubated mixture resulting from the oxidation of the chromogenic substrate, catalyzed by the peroxidase;
(c) stabilizing the chromophore in said incubated mixture either after further oxidizing the residual chromogenic substrate in said incubated mixture to form chromophore by adding a peroxidase or a peroxidatively active substance, or after supplementing said incubated mixture with a chromophore prepared by oxidizing a chromogenic substrate which is identical to the chromogenic substrate used in step (a), to produce a stabilized mixture;
(d) bringing said stabilized mixture into contact with a mercury-containing compound, to produce a reaction mixture; and
(e) determining the penicillinase activity by measuring the decolorization of the chromophore in said reaction mixture, caused by the open beta-lactam ring end product resulting from penicillinase hydrolysis of said penicillin.

15. The method of claim 14 wherein the N-alkyl derivative of p-phenylenediamine is N,N,N',N'-tetramethyl-p-phenylenediamine, and the 3,3',5,5'-tetraalkyl derivative of benzidine is 3,3',5,5'-tetramethylbenzidine.

16. The method of claim 14 wherein said chromophore in said incubated mixture or said supplemented incubated mixture is stabilized with a catalase or sodium dodecyl sulfate.

17. The method of claim 14 wherein the mercury-containing compound is either an inorganic mercuric compound, or an organomercury compound with the common formula, —C—Hg—A, in which Hg is concomitantly bonded to a carbon in an aliphatic chain, in an aromatic ring, or in a heterocyclic ring and to an anion.

18. The method of claim 17 wherein the inorganic mercuric compound is selected from a group consisting of mercuric acetate, mercuric bromide, mercuric chloride, mercuric nitrate, mercuric sulfate, and mercuric thiocyanate; while the organomercury compound is selected from a group consisting of ethylmercuric chloride, mersalyl acid, thimerosal, p-aminophenylmercuric acetate, p-chloromercuribenzoic acid, sodium p-chloromercuriphenylsulfonate, sodium p-hydroxymercuribenzoate, sodium 2-(hydroxymercuri)benzoate, sodium p-hydroxymercuriphenylsulfonate, phenylmercuric acetate, and sodium 5-mercuri-2'-deoxyuridine 5'-triphosphate.

19. The method of claim 14 wherein said reaction mixture contains the mercury-containing compound in a final concentration ranging from 0.005 nM to 3 mM, and has a pH ranging from 3.5 to 8.0.

* * * * *